US00PP22657P2

(12) United States Plant Patent
Smith

(10) Patent No.: US PP22,657 P2
(45) Date of Patent: Apr. 17, 2012

(54) ***CHRYSANTHEMUM* PLANT NAMED 'SYNJAC ORANFUS'**

(50) Latin Name: *Chrysanthemum×morifolium*
Varietal Denomination: Synjac Oranfus

(75) Inventor: Mark A. Smith, Alva, FL (US)

(73) Assignee: Syngenta Crop Protection AG, Basel (CH)

( * ) Notice: Subject to any disclaimer, the term of this patent is extended or adjusted under 35 U.S.C. 154(b) by 32 days.

(21) Appl. No.: 12/925,287

(22) Filed: Oct. 18, 2010

(51) Int. Cl.
*A01H 5/00* (2006.01)

(52) U.S. Cl. ..... Plt./287

(58) Field of Classification Search ..... Plt./287, Plt./290, 296, 298
See application file for complete search history.

*Primary Examiner* — June Hwu
(74) *Attorney, Agent, or Firm* — S. Matthew Edwards

(57) ABSTRACT

A new *Chrysanthemum* plant named 'Synjac Oranfus' particularly distinguished by the medium sized flowers with orange-red and yellow two-toned colored ray florets, dark yellow-green foliage, uniform ball-shaped plant habit and a natural season flowering about mid-September.

1 Drawing Sheet

Latin name of the genus and species of the plant claimed: *Chrysanthemum×morifolium.*

Varietal denomination: 'Synjac Oranfus'.

BACKGROUND OF THE NEW PLANT

The present invention comprises a new *Chrysanthemum*, botanically known as *Chrysanthemum×morifolium*, and hereinafter referred to by the variety name 'Synjac Oranfus'.

'Synjac Oranfus' is a product of a planned breeding program. The new cultivar has medium sized flowers with orange-red and yellow two-toned colored ray florets, dark yellow-green foliage, uniform ball-shaped plant habit and a natural season flowering about mid-September.

'Synjac Oranfus' originates as a natural whole plant mutation of 'Yojacqueline', U.S. Plant Pat. No. 18,927, and was discovered outdoor in a large quantity trial format and selected by the inventor as a single flowering plant within a population of the parent cultivar in a controlled breeding program in Alva, Fla. in November 2006. The parent cultivar 'Yojacqueline' has two-toned pink ray florets and has a slower flowering response in shaded crops.

The first act of asexual reproduction of 'Synjac Oranfus' was accomplished when vegetative cuttings were propagated from the initial selection in December 2006 in a controlled environment in Alva, Fla.

BRIEF SUMMARY OF INVENTION

Horticultural examination of plants grown from cuttings of the plant initiated in December 2006 and continuing thereafter, has demonstrated that the combination of characteristics as herein disclosed for 'Synjac Oranfus' are firmly fixed and are retained through successive generations of asexual reproduction.

'Synjac Oranfus' has not been observed under all possible environmental conditions. The phenotype may vary significantly with variations in environment such as temperature, light intensity and day length.

A Plant Breeder's Right for this cultivar was applied for in Canada on Oct. 30, 2009 (09-6766). 'Synjac Oranfus' has not been made publicly available more than one year prior to the filing of this application.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawing shows typical flower and foliage characteristics of 'Synjac Oranfus' with colors being as true as possible with an illustration of this type.

The photographic drawing shows a flowering potted plant of the new variety growing in a 9 inch pot in an outdoor trial in Monroeville, N.J. in September 2008. This plant is about 12 weeks old.

DETAILED BOTANICAL DESCRIPTION

The plant descriptions and measurements were taken in Gilroy, Calif. in the later summer 2009 under natural light. These plants used for the descriptions were about 10 weeks old.

Color references are made to The Royal Horticultural Society Colour Chart (R.H.S.) 2001.

TABLE 1

DIFFERENCES BETWEEN THE NEW VARIETY 'SYNJAC ORANFUS' AND A SIMILAR VARIETY: 'ORANGE URANO' (U.S. Plant Pat. No. 13,019)

| | 'Synjac Oranfus' | 'Orange Urano' (U.S. Plant Pat. No. 13,019) |
|---|---|---|
| Flower size: | Smaller | Larger |
| Disc floret quantity: | Fewer | More |
| Natural season flowering response: | Several days slower | Faster |

Plant:
*Form, growth and habit*.—Herbaceous decorative garden type; stems upright and outwardly spreading, freely branching, strong and moderately vigorous growth habit.
*Plant height*.—About 10-12 cm.
*Plant height* (*inflorescence included*).—13-15 cm.
*Plant width*.—20-23 cm.
*Garden performance and tolerance to weather*.—Very good.

Roots:
*Number of days to initiate roots*.—4 days at about 22 degrees C.
*Number of days to produce a rooted cutting*.—10-12 days at 22 degrees C.
*Type*.—Fine, fibrous, free branching.
*Color*.—RHS N155B but whiter.

Foliage:
*Arrangement*.—Alternate, simple.
*Immature, leaf color, upper surface*.—Closest to RHS 147A.
*Lower surface*.—Closest to RHS 137A.
*Mature, leaf color, upper surface*.—Closest to RHS 147A.
*Lower surface*.—Closest to RHS 137A.
*Length*.—2.5-2.7 cm.
*Width*.—2.5-2.7 cm.
*Shape*.—Squat ovate.
*Base shape*.—Attenuate.
*Apex shape*.—Mucronulate.
*Margin*.—Palmately lobed; very slightly and irregularly serrulate.
*Texture, upper surface*.—Bifid T-shaped hairs.
*Lower surface*.—Bifid T-shaped hairs.
*Color of veins, upper surface*.—RHS 138A.
*Color of veins, lower surface*.—RHS 138A.
*Petiole color*.—RHS 138A.
*Length*.—0.6-0.8 cm.
*Diameter*.—0.2 cm.
*Texture*.—Bifid T-shaped hairs.

Stem:
*Quantity of main branches per plant*.—About 10-12.
*Color of stem*.—Closest to RHS 138A.
*Length of stem*.—7-9 cm.
*Diameter*.—0.3 cm.
*Length of internodes*.—0.5 cm.
*Texture*.—Bifid T-shaped hairs.
*Color of peduncle*.—RHS 138A.
*Length of peduncle*.—2.5-5.5 cm.
*Peduncle diameter*.—0.15 cm.
*Texture*.—Bifid T-shaped hairs.

Inflorescence:
*Type*.—Compositae type, solitary inflorescences (decorative-type) borne terminally above foliage, ray florets arranged acropetally on a capitulum.
*Natural season flowering*.—Mid-September.
*Quantity of inflorescences per plant*.—About 45 inflorescences plus about 50 buds.
*Lastingness of individual blooms on the plant*.—About 3-4 weeks.
*Fragrance*.—Slightly spicy.

Bud (just when opening/showing color):
*Color*.—About RHS 9B basally with between RHS 35A and RHS 35B apex.
*Length*.—0.7-1.4 cm.
*Width*.—0.7-0.9 cm.
*Shape*.—Oblate.

Immature inflorescence:
*Diameter*.—3.0 cm.
*Color of ray florets, upper surface*.—RHS 9B basally, with between RHS 35A and RHS 35B but some are almost RHS 50B at the apex.
*Lower surface*.—RHS 9D with about RHS 51D at the apex.

Mature inflorescence:
*Diameter*.—About 4.0 cm.
*Depth*.—2.0 cm.
*Total diameter of 'disc'*.—0.5 cm.
*Receptacle height*.—0.4-0.45 cm.
*Receptacle diameter*.—0.3-0.4 cm.

Ray florets:
*Average quantity of florets*.—About 60 in numerous whorls.
*Color of florets, upper surface*.—Closest to RHS 9B to RHS 9C basally with about RHS 35 B to RHS 35C at the apex, and some are about RHS 50 B to RHS 50C at the apex.
*Lower surface*.—Closest to RHS 9D with about RHS 51D at the apex.
*Length*.—1.5-2.0 cm.
*Width*.—0.5-0.6 cm.
*Shape*.—Oblong.
*Apex shape*.—Praemorse.
*Margin*.—Entire.
*Texture, upper surface*.—Papillose.
*Lower surface*.—Papillose.

Disc florets:
*Average quantity of florets*.—About 5-10.
*Color of florets*.—RHS 1B.
*Length*.—0.2-0.25 cm.
*Width*.—0.1 cm.
*Shape*.—Tubular, elongated.
*Apex shape*.—Acute, 5 pointed.

Phyllaries:
*Quantity*.—About 23-25.
*Color, upper surface*.—RHS 146C.
*Lower surface*.—RHS 146C.
*Length*.—0.6-0.7 cm.
*Width*.—0.2-0.3 cm.
*Shape*.—Lanceolate.
*Apex shape*.—Acute.
*Based*.—Fused.
*Margins*.—Entire and papery.
*Texture, upper surface*.—Glabrous.
*Lower surface*.—Bifid T-shaped hairs.

Reproductive organs:
*Pistil*.—1.
*Found on both florets*.—Yes.
*Length*.—0.3-0.4 cm.
*Style color*.—RHS 1C.
*Style length*.—0.2-0.3 cm.
*Stigma color*.—RHS 1B.
*Stigma shape*.—Bi-parted.
*Ovary color*.—RHS155C.
*Stamens*.—1.
*Found on disc florets only*.—Yes.
*Color of filaments*.—RHS 1C.
*Length filaments*.—0.2 cm.
*Anther color*.—RHS 3A.
*Anther length*.—0.1 cm.

*Anther shape*.—Oblong.

*Color of pollen*.—RHS 6B.

*Pollen amount*.—Moderate.

*Fertility/seed set*.—Has not been observed on this hybrid.

Disease/pest resistance: Disease/pest resistance has not been observed on this hybrid.

What is claimed is:

1. A new and distinct variety of *Chrysanthemum* plant named 'Synjac Oranfus' substantially as illustrated and described herein.

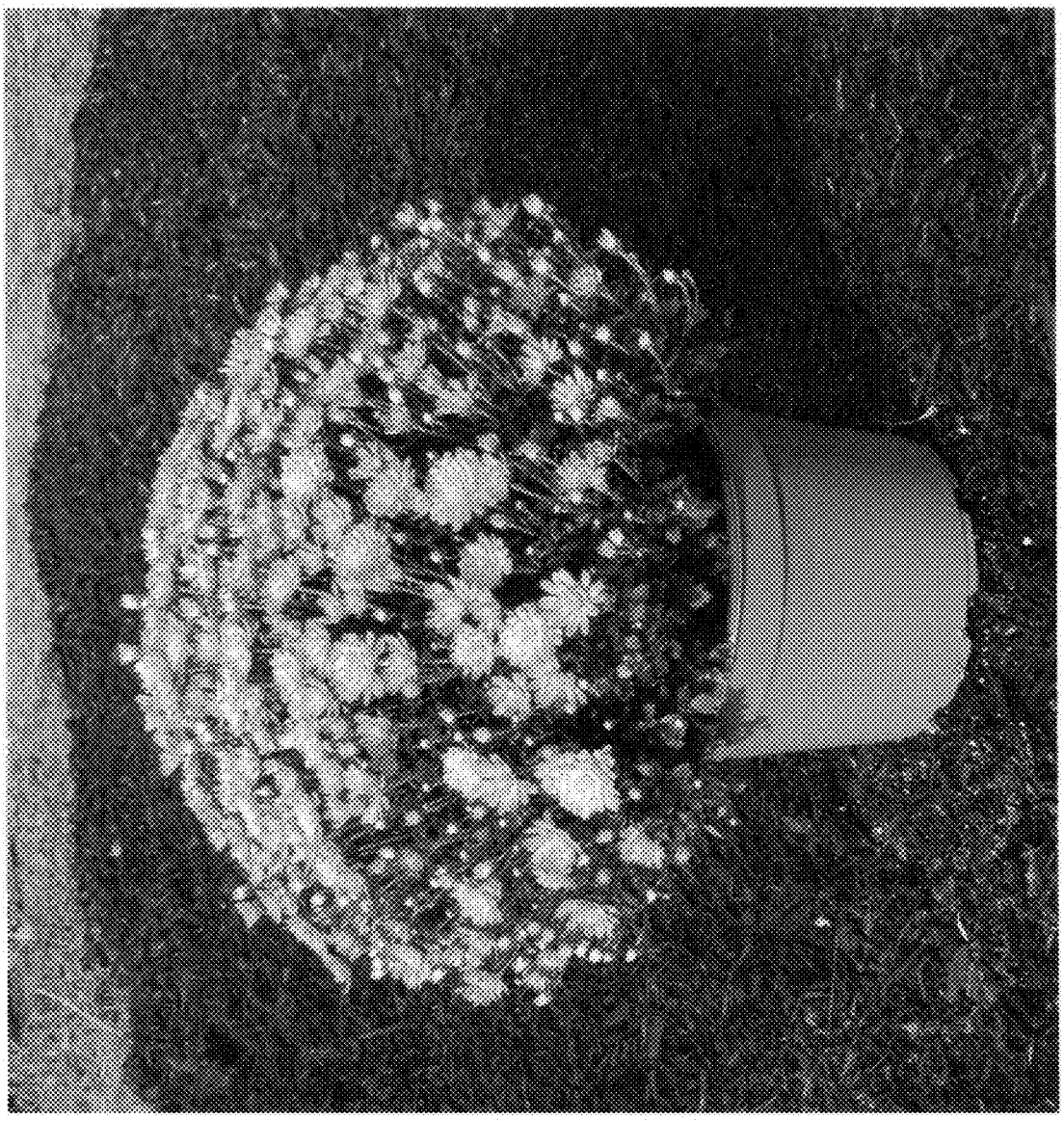

* * * * *